(12) United States Patent
Kanerva et al.

(10) Patent No.: US 8,634,631 B2
(45) Date of Patent: Jan. 21, 2014

(54) ODONTOLOGICAL IMAGING APPARATUS

(75) Inventors: Jukka Kanerva, Helsinki (FI); Henri Veistera, Helsinki (FI); Jaakko Lahelma, Helsinki (FI)

(73) Assignee: Planmeca Oy, Helsinki (FI)

( * ) Notice: Subject to any disclaimer, the term of this patent is extended or adjusted under 35 U.S.C. 154(b) by 115 days.

(21) Appl. No.: 13/425,912

(22) Filed: Mar. 21, 2012

(65) Prior Publication Data
US 2012/0243762 A1 Sep. 27, 2012

(30) Foreign Application Priority Data
Mar. 21, 2011 (FI) .................................... 20110106

(51) Int. Cl.
*G06K 9/00* (2006.01)

(52) U.S. Cl.
USPC ........................... 382/132; 250/493.1; 378/11

(58) Field of Classification Search
USPC ................ 382/100, 128, 129, 130, 131, 132; 128/922; 378/2–27, 38–40, 167–188; 250/493.1, 503.1, 505.1
See application file for complete search history.

(56) References Cited

U.S. PATENT DOCUMENTS

| | | | | |
|---|---|---|---|---|
| 4,852,134 A * | 7/1989 | Kinanen et al. | ................ | 378/38 |
| 5,224,140 A * | 6/1993 | Virta et al. | ................ | 378/38 |
| 5,511,106 A * | 4/1996 | Doebert et al. | ................ | 378/146 |
| 7,058,158 B2 * | 6/2006 | Sako | ................ | 378/17 |
| 7,711,085 B2 * | 5/2010 | Suzuki et al. | ................ | 378/39 |
| 8,290,119 B2 * | 10/2012 | Tancredi et al. | ................ | 378/38 |
| 2003/0129565 A1 | 7/2003 | Kaza | | |
| 2005/0084144 A1 * | 4/2005 | Feldman | ................ | 382/128 |
| 2006/0050846 A1 * | 3/2006 | Sako | ................ | 378/62 |
| 2008/0056439 A1 * | 3/2008 | Thompson et al. | ................ | 378/15 |
| 2009/0041191 A1 | 2/2009 | Suzuki et al. | | |
| 2010/0124731 A1 * | 5/2010 | Groscurth et al. | ................ | 433/213 |
| 2011/0059413 A1 | 3/2011 | Schutyser et al. | | |
| 2012/0039435 A1 * | 2/2012 | Arai et al. | ................ | 378/11 |

FOREIGN PATENT DOCUMENTS

JP 2007061592 A 3/2007

OTHER PUBLICATIONS

Hsieh, J., "Computed Tomography: Principles, Design, Artifacts and Recent Advantages", year 2009.
Bushberg et al., "The essential physics of medical imaging", year 2002.
Padge, D., The virtual autopsy: The doctor will scan you now, Aug./Sep. 2008.
Swennen, G. "A cone beam CT based technique to augment the 3D virtual skull model with a detail dental surface", year 2009.
Filip Schutyuser, "Robust visualization of the dental occlusion by a double scan procedure", year 2005.

* cited by examiner

*Primary Examiner* — Anand Bhatnagar
(74) *Attorney, Agent, or Firm* — Fay Sharpe LLP (57) ABSTRACT

A dental CT apparatus includes a control system arranged to move a radiation source and an imaging sensor on the opposite sides of an imaging station. The control system includes at least a first imaging mode designed for imaging patients and means for selecting at least one second imaging mode in which the source of radiation and the imaging sensor are driven during an exposure at an angular velocity of less than 4 degrees/second. A digital three dimensional models of teeth are generated based on imaging impressions or models of teeth by a CT apparatus provided with at least one specific imaging mode for the purpose.

27 Claims, 4 Drawing Sheets

ODONTOLOGICAL IMAGING APPARATUS

FIELD

The present inventive subject matter relates generally to the art of odontological imaging. Particular but not exclusive relevance is found in connection with an odontological imaging apparatus and/or method, and accordingly the present specification makes reference thereto. It is to be appreciated however that aspects of the present inventive subject matter are also equally amenable to other like applications.

BACKGROUND

Medical X-ray imaging has a long history. The earliest techniques were based on transilluminating an object being imaged. In transillumination, all the anatomies of the volume being imaged possibly overlapping in the direction of radiation are imaged on top of each other. In order to solve this problem, layer or so-called tomographic imaging was later developed, by means of which it is possible to get a desired layer of the object to become imaged more clearly by causing blurring in the other layers of the object in the image being formed. Blurring is accomplished by changing the relative position of the imaging means and the object during an imaging event, depending on the imaging procedure, either during irradiation or between individual irradiations.

Later on, and especially along with the advancement of computers and digital imaging, a great number of different tomographic imaging techniques and devices have been developed. In the field of odontology, one generally uses, in addition to intra-oral and cephalometric imaging, which are simpler as far as imaging technology is concerned and are realised by transillumination imaging, among other things, so-called panoramic imaging in which, typically, a layer comprising the whole dental arch is imaged on a plane. Lately, an interest has further started to arise in applying computer or computed) tomography (CT), used earlier predominantly in the clinical environment, also in the field of odontology.

Several different CT imaging techniques are known today. In CT imaging, the volume being imaged is irradiated from different directions and, from the data thus acquired, a desired two- or three-dimensional image is reconstructed afterwards. As far as general principles of computer tomography and its different applications are concerned, reference can be made to, e.g., Computed Tomography: Principles, Design, Artifacts and Recent Advantages, Jian Hsieh, SPIE PRESS, 2003, Bellingham, Wash., USA.

One form of computer tomography is the so-called cone beam CT (CBCT) in which one uses, as a distinction from the narrow beam used e.g. in panoramic imaging, a cone-like beam substantially the size of the dimensions of the volume to be imaged and, instead of a slot sensor, a detector the size of which corresponds to the size of the cone in question. Compared to several more conventional CT imaging technologies, by CBCT technology one is able to reach significantly smaller radiation doses and shorter imaging times.

In general, for the X-ray imaging of humans and live patients, it is generally desirable to comply with the so-called ALARA (as low as reasonably achievable) principle. This means that the imaging is done with a radiation dose as small as possible to make a diagnosis—that is, by an imaging procedure producing a radiation dose as small as possible which still enables the diagnosis. Thin principle can be an impediment for utilising the possibilities basically offered by computer tomography in practice.

However, problems in connection with imaging patients can be caused by the patient moving during the imaging process. For this reason, in connection with imaging patients one typically tries to realize the imaging process as short as possible, within conditions dictated by the imaging process itself.

In connection with odontological operations, such as when planning operations related to orthodontic treatment, prosthodontics and surgical operations, one often utilises plaster casts of the teeth or other physical models by means of which it is possible to e.g. manually perform tooth transplantations and design occlusion corrections, crowns and bridges. It is also known to scan these physical models, as well as impressions of the teeth from which the actual model will be made, into digital format. Such a digital model can be programmatically combined to an X-ray image of the patient, whereby it is e.g. possible to combine information on both the patient's teeth and soft tissue of the oral area in the same image. This offers the clinical specialist opportunities to transfer from manual work phases towards digital ones and, thus, towards more comprehensive and detailed treatment planning.

A factor which hinders digitising of models and impressions becoming more common is that producing 3D image information requires use of a device particularly designed for the purpose. However, it is not necessarily reasonable for a dentist to invest in such devices. Accordingly, to be able to utilise the advantages of digitalization discussed above, one must often resort to outsourcing the scanning service.

Accordingly, a new and/or improved odontological imaging apparatus and/or method is disclosed which addresses the above-referenced problem(s) and/or others.

SUMMARY

This summary is provided to introduce concepts related to the present inventive subject matter. This summary is not intended to identify essential features of the claimed subject matter nor is it intended for use in determining or limiting the scope of the claimed subject matter.

One object is to advance the state of art related on the one hand to odontological X-ray apparatuses, on the other hand to the 3D imaging of physical impressions and models of the teeth. Through the use of various embodiments, e.g. a dental clinic may opt not to separately invest in an apparatus dedicated to scanning impressions and models, which lowers the threshold of being able to utilise anatomy information in digital format in planning dental care. The tooth and soft tissue models producible by the apparatus described herein can optionally, in addition to the above listed applications enabled by digitalisation of models, be utilised e.g. in 3D dental implant design.

Some characteristics of the inventive subject matter are described in the accompanying patent claims. Specifically, in one embodiment, an odontological computer tomography apparatus is used as a platform, wherein imaging of impressions and models is arranged to be implemented. In the suitable embodiments, the odontological computer tomography apparatus is arranged, in addition to one or more patient-diagnostic imaging modes, with at least one imaging mode particularly intended for the imaging of dental impressions and models. One characteristic of such an imaging mode is that in realizing it, both the abovementioned ALARA principle and the possible problems caused by patient movement can be forgotten whereby imaging parameters, such as imaging time, do not have to be limited by the conditions set when imaging patients but they can be optimised from the viewpoint of obtaining the best possible image quality.

More specifically, in accordance with one exemplary embodiment, an odontological X-ray imaging apparatus is arranged to enable at least computed tomography imaging. The apparatus includes: an imaging station in which is selectively placed a subject being imaged by the apparatus; a radiation source and a collimator structure which output x-ray radiation in a shape of a cone beam in a direction of the imaging station; an imaging sensor including a two dimension array of x-ray detecting elements, the imaging sensor being arranged across the imaging station from the radiation source; a construction including an actuator operative to rotate the radiation source and the imaging sensor about the imaging station, at least during an imaging exposure in which x-ray radiation is output from the radiation source and detected by the imaging sensor; and a control system for controlling operation of at least one of the actuator, the radiation source and the imaging sensor, according to at least one of two operative imaging modes, including a first imaging mode for imaging a subject's actual odontological anatomy and a second imaging mode for imaging a physical representation of a subject's odontological anatomy. Suitably, when operating in the second imaging mode, the control system controls operation of the actuator during an imaging exposure so that the radiation source and the imaging sensor are rotated about the imaging station at an angular velocity of less than approximately 4 degrees/second.

Furthermore, when operating in the second imaging mode, the control system may control operation of the actuator during an imaging exposure so that the radiation source and the imaging sensor are rotated about the imaging station at an angular velocity on an order of 2 degrees/second or slower.

Furthermore, when operating in the second imaging mode, the control system may control the imaging sensor such that during an exposure, more than approximately 500 images are taken at different projection angles.

Furthermore, when operating in the second imaging mode, the control system may control operation of the actuator during an imaging exposure so that the radiation source and the imaging sensor are rotated about the imaging station through a complete angle of rotation on the order of approximately 200 degrees.

Furthermore, when operating in the second imaging mode, the control system may control the imaging sensor such that during an exposure, on the order of approximately 1,000 images are taken at different projection angles within the complete angle of rotation.

Furthermore, when operating in the second imaging mode, the control system may control operation of the actuator during an imaging exposure so that the radiation source and the imaging sensor are rotated about the imaging station through a complete angle of rotation on the order of appropriately 200 to 360 degrees in an imaging process lasting at least on the order of 1 to 2 min.

Furthermore, when operating in the second imaging mode, the control system may control the imaging sensor such that individual images are read out from the imaging sensor without summing up information of adjacent pixels before reading out the information or during read-out.

Furthermore, when operating in the second imaging mode, the control system may control operation of the actuator during an imaging exposure so that the radiation source and the imaging sensor are rotated about the imaging station such that a projection on the imaging sensor produced by a beam of a point or item located in an object being imaged moves during taking one image at most a distance which substantially equals a dimension of a pixel of the imaging sensor in the direction of movement the imaging sensor.

Furthermore, when operating in the second imaging mode, the control system may control an operation of the apparatus such that a dose area product (DAP) produced by the radiation source on a cross section with respect to a central axis of the beam, when considering a beam having an area of 0.02 m2 at a distance of 0.6 m from a focus of the source of radiation, is larger than approximately 200 μGym2.

Furthermore, when operating in the second imaging mode, the control system may control an operation of the apparatus such that a radiation dose (Gray) produced by the radiation source substantially at a location of the imaging station is on the order of approximately 40 mGy or more.

Furthermore, when operating in the second imaging mode, the control system may control an operation of the apparatus such that a radiation dose produced by the radiation source is on the order of twice as high or higher than that produced when operating in the first imaging mode.

Furthermore, the apparatus may be arranged to receive at least one support comprising a platform positioned within the imaging station when the support is installed, the platform arranged to hold thereon the physical representation of a subject's odontological anatomy.

Furthermore, the physical representation may include at least one of a negative dental impression or a positive dental model.

Furthermore, when the platform is positioned in the imaging station, it may inhibit a subject from positioning their actual odontological anatomy substantially within the imaging station.

Furthermore, the control system may be implemented so that the second imaging mode is inhibited from selection when the support is not installed.

Furthermore, the control system may be implemented so that the second imaging mode is enabled for selection only when the support is installed.

Furthermore, the apparatus may be arranged to receive at least one support which positions a subject's actual odontological anatomy within the imaging station and the control system may be implemented so that the second imaging mode is inhibited from selection when the support is installed.

Furthermore, the control system may be implemented such that the second imaging mode can be used only when specifically enabled.

In accordance with another exemplary embodiment, an odontological X-ray imaging apparatus is arranged to enable at least computed tomography imaging. The apparatus includes: an imaging station in which is selectively placed a subject being imaged by the apparatus; a radiation source and a collimator structure which outputs x-ray radiation in a shape of a cone beam in a direction of the imaging station; an imaging sensor including a two dimension array of x-ray detecting elements, the imaging sensor being arranged across the imaging station from the radiation source; a construction including an actuator operative to rotate the radiation source and the imaging sensor about the imaging station, at least during an imaging exposure in which x-ray radiation is output from the radiation source and detected by the imaging sensor; and a control system for controlling operation of at least one of the actuator, the radiation source and the imaging sensor, according to at least one of two operative imaging modes, including a first imaging mode for imaging a subject's actual odontological anatomy and a second imaging mode for imaging a physical representation of a subject's odontological anatomy. Suitably, the apparatus is arranged to receive a selected one of at least two supports, including a first support which positions a subject's actual odontological anatomy within the imaging station and a second support which positions a physical representation of a subject's odontological anatomy within the imaging station, the physical representation including at least one of a negative dental impression or a positive dental model; and when operating in the second imaging mode, the control system controls operation of the actuator during an imaging exposure so that the radiation source and the imaging sensor are rotated about the imaging station at an angular velocity of loss than approximately 4 degrees/second.

In accordance with still another exemplary embodiment, a method is provided for creating a three-dimensional digital model of one or more teeth. The method includes: obtaining a physical representation of a patient's teeth, the physical representation of the teeth being at least one of a three-dimensional negative impression of the teeth or a three-dimensional positive model of the teeth; placing the physical representation of the teeth in an imaging station of an odontological X-ray imaging apparatus arranged and constructed for cone beam CT imaging of a live patient; imaging the physical representation of the teeth by an imaging mode different from any imaging mode of the imaging apparatus arranged for the imaging of live patients; and generating the three-dimensional digital model of the teeth by processing image data detected upon imaging the physical representation of the teeth with the imaging apparatus.

Furthermore, the imaging apparatus may be selectively operable in one of two modes, including a first mode for imaging a live patient's actual teeth and a second mode for imaging the physical representation of the teeth, and the method may further include selecting the appropriate mode.

Furthermore, the method may additionally include connecting a platform to the imaging apparatus, the platform being arranged to hold the physical representation of the teeth within the imaging station.

Furthermore, the method may additionally include: detecting whether or not the platform is connected to the imaging apparatus; and automatically regulating an ability to select the second mode based on the detecting.

Furthermore, when the platform is connected to the imaging apparatus, it may at least partially inhibit a live patient from positioning their actual teeth substantially within a path of radiation extending through the imaging station.

In yet one more exemplary embodiment, a method is provided for obtaining image data to create a three-dimensional image of odontological structures. The method includes: providing an odontological X-ray imaging apparatus including a radiation source and an imaging sensor arranged at a distance from each other and rotatable about an imaging station, the apparatus being selectively operable in one of at least two modes including a first mode for imaging a subject's actual odontological anatomy and a second mode for imaging a physical representation of a subject's odontological anatomy, the physical representation including at least one of a negative dental impression or a positive dental model; having selectively connected to the imaging apparatus one of a patient support device that supports actual odontological anatomy to be imaged within the imaging station or a platform that holds at least a portion of the physical representation to be imaged within the imaging station; detecting if the patient support device or the platform is connected to the imaging apparatus; and regulating an ability to select the operative mode of the apparatus based upon the detecting.

Furthermore, operation the apparatus in the second mode may be inhibited if it is detected that the platform is not connected to the imaging apparatus.

Furthermore, wherein operation of the apparatus in the second mode may be inhibited if it is detected that the patient support device is connected to the imaging apparatus.

Numerous advantages and benefits of the inventive subject matter disclosed herein will become apparent to those of ordinary skill in the art from the present specification.

Next, preferable and/or other embodiments will be described in more detail and also with reference to the figures.

BRIEF DESCRIPTION OF FIGURES

The following detailed description makes reference to the figures in the accompanying drawings. However, the inventive subject matter disclosed herein may take form in various components and arrangements of components, and in various steps and arrangements of steps. The drawings are only for purposes of illustrating exemplary and/or preferred embodiments and are not to be construed as limiting. Further, it is to be appreciated that the drawings may not be to scale.

DETAILED DESCRIPTION

Figure 1:
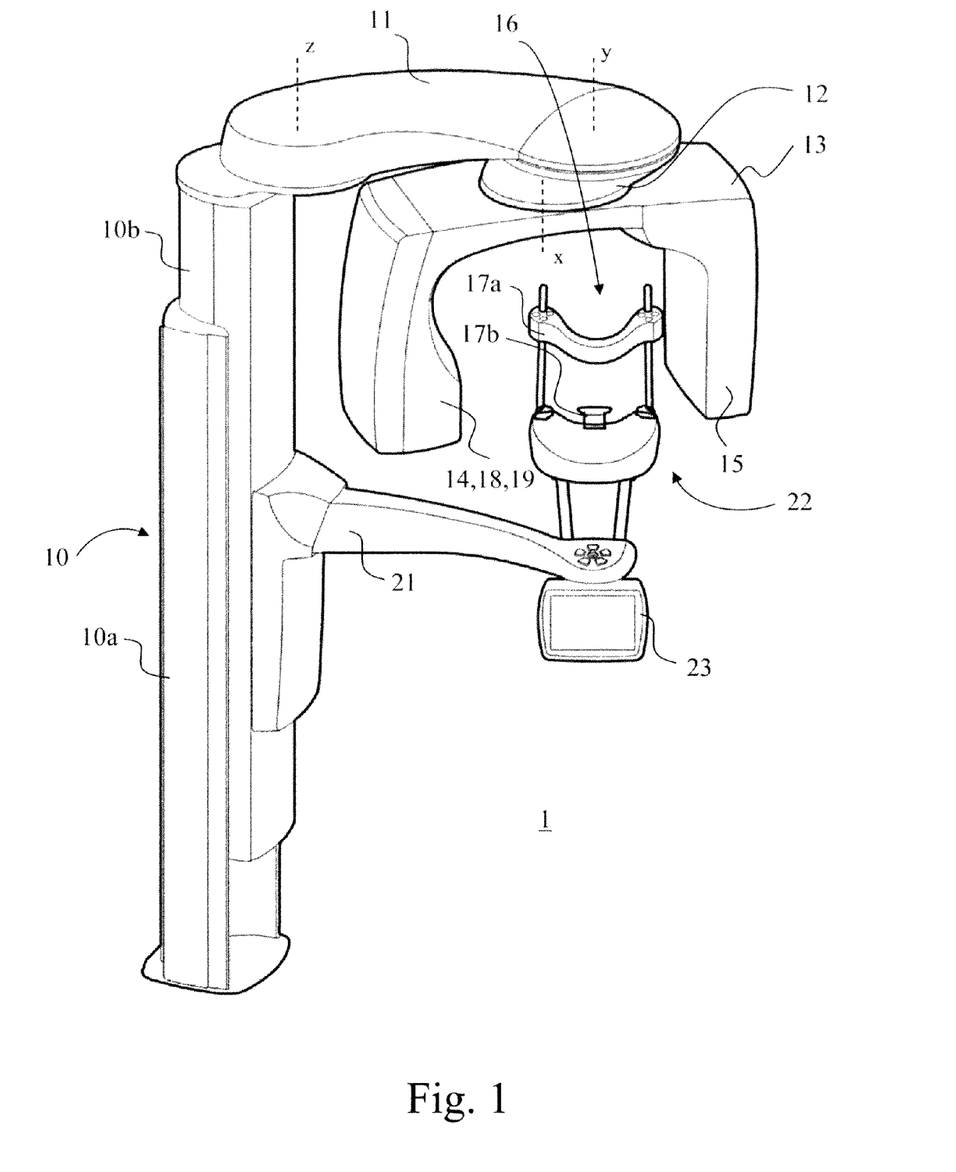
FIG. 1 shows by way of an example a general view of an imaging apparatus which is suitable for practicing aspects of the present inventive subject matter.

FIG. 1 shows an imaging apparatus 1 suitable for practicing aspects of the present inventive subject matter. The apparatus 1 includes a housing part 10 and a set of imaging arms arranged to protrude from it, which set comprises three imaging arm parts 11, 12, 13. The third of these arm parts 13 is arranged to rotate or pivot (e.g., about an axis x) with respect to the second arm part 12; the second arm part 12 is arranged to rotate or pivot (e.g., about an axis y) with respect to the first arm part 11; and the first arm part 11 is arranged to rotate or pivot (e.g., about an axis z) with respect to the housing part 10. The third arm part 13 supports imaging means including a source of radiation 14 (e.g., such as an X-ray tube) and an imaging sensor 15 having a two-dimensional pixel matrix. Suitably, the radiation source 14 and the sensor 15 may be arranged within a cover of the arm part 13 and at a distance from each other. Also optionally within the cover of the arm part 13, and proximate to the radiation source 14, there is further arranged a collimator structure 18 for limiting radiation produced by the radiation source 14 to a beam of desired size and shape, and optionally a filter 19 for adjusting a spectrum of the beam to be as desired. The beam may be a two dimensional cone beam used in so-called cone beam computed tomography.

As shown, the imaging apparatus 1 of FIG. 1 further includes a second arm part 21 protruding from the housing part 10 and arranged to support patient support means 22. Suitably, the second arm part 21 positions the patient support means 22 with respect to the set of imaging arms 11, 12, 13 of the apparatus, such that the patient support means 22 is located substantially in an area between the radiation source 14 and the sensor 15, which area constitutes an imaging station 16. While in practice different patient support means 22 may be utilized, FIG. 1 shows a band 17a arranged to receive and/or support a patient's forehead and a bite block 17b on to which a patient may bite.

As shown in FIG. 1, on the arm part 21 supporting the patient support means 22, there is further arranged a control panel or other like user interface 23 via which the different functions of the imaging apparatus 1 can be controlled. In practice, the imaging apparatus 1 also includes actuators and a control system and routines for moving the imaging arm parts 11, 12, 13 of the apparatus to a desired position and in a desired way and, further, for controlling functions of the radiation source 14 and the imaging sensor 15.

While FIG. 1 shows one embodiment suitable for practicing aspects of the present inventive subject matter, other types of imaging apparatuses (other than the one shown in FIG. 1) may likewise be employed. For example, the first imaging arm part 11 can be attached to a ceiling or a wall, whereby the apparatus does not have to include an actual housing part 10. Then, the patient support means 22 can be arranged attached to some other structure than the housing part 10. The set of imaging arms 11, 12, 13 can also have less than three arm parts. For example, only one arm part 13 may be provided which is able to turn or rotate or pivot with respect to a physical or virtual axis of rotation.

Optionally, the set of imaging arms 11, 12, 13 of the imaging apparatus 1 also has freedom of movement in a vertical direction. As shown in FIG. 1, this may be accomplished with a multipart housing 10. That is to say, the housing 10 may include parts 10a and 10b, where the set of imaging arms 11, 12, 13 are supported from the housing part 10b. The housing part 10b may then be vertically movable with respect to the housing part 10a, and hence the set of imaging arms 11, 12, 13 are provided freedom of movement in the vertical direction. Optionally, the arm 21 is also supported from the housing part 10b such that the patient support means are made to move vertically along with the vertical movement of the set of imaging arms 11, 12, 13. It is also possible to arrange for the set of imaging arms 11, 12, 13 and the arm part 21 supporting the patient support means 22, a vertical degree of freedom of motion independent from each other. For example, this may be accomplished by having the arm part 21 movable in a vertical direction with respect to the housing part 10b on which it is supported.

Figure 2A:
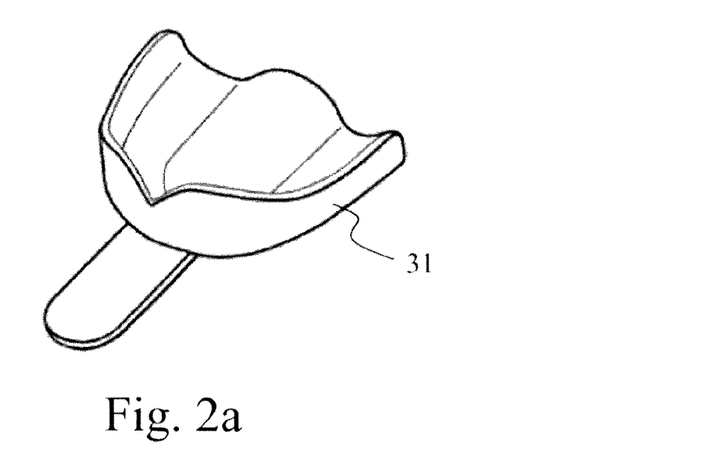
FIGS. 2a, 2b and 2c show an impression tray used in connection with obtaining a physical impression of teeth, an impression of a dental arch in such tray and a physical model made based on such impression.
Figure 2B:
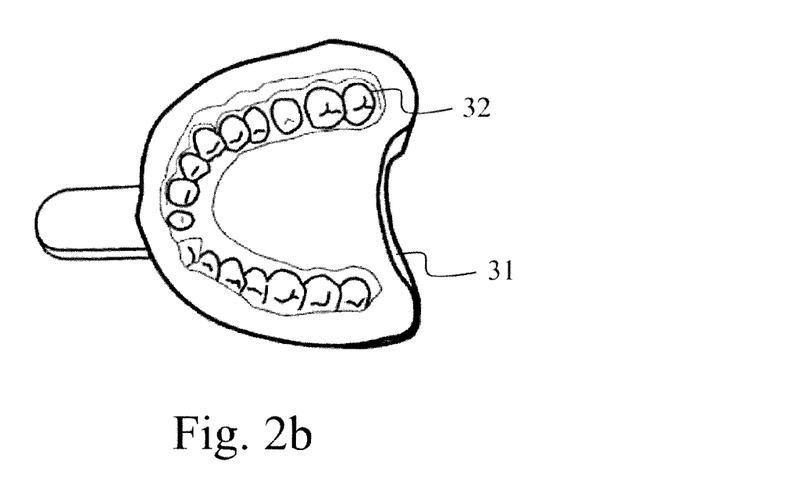
Figure 2C:
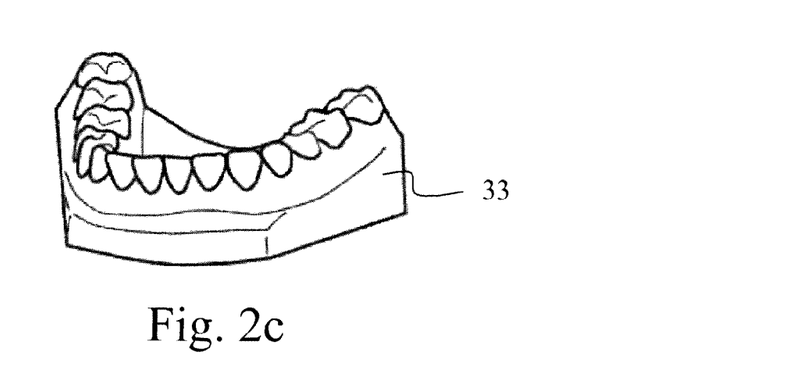

FIGS. 2a, 2b and 2c show an impression tray 31 used in connection with making a physical impression of a patient's teeth, a physical impression 32 (i.e., "a negative model") of a dental arch on such a tray 31, and a physical model 33 made based on such an impression 32. The impression of the teeth can be provided by filling the impression tray 31 according to FIG. 2a with a hardening material and by pressing the tray 31 filled with such a mass against the teeth of the patient's upper or lower jaw. The model 33 of the teeth according to FIG. 2c an then be cast by filling the hardened negative model 32 of the dental arch, e.g., with a mass of plaster.

Figure 3A:
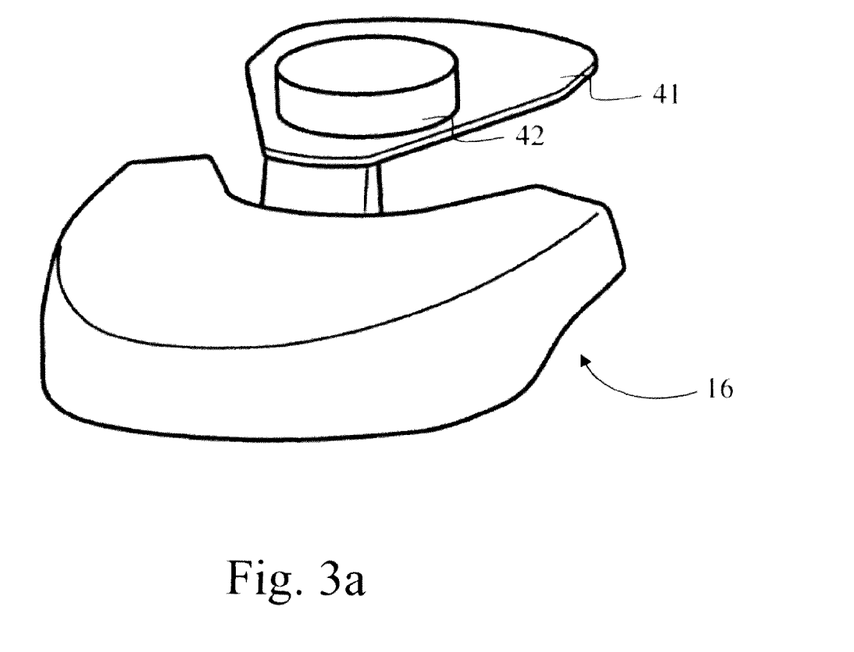
FIGS. 3a and 3b show an imaging platform selectively attachable to the apparatus of FIG. 1, e.g., to hold a physical tooth impression or model positioned on the platform in an imaging station of the apparatus.
Figure 3B:
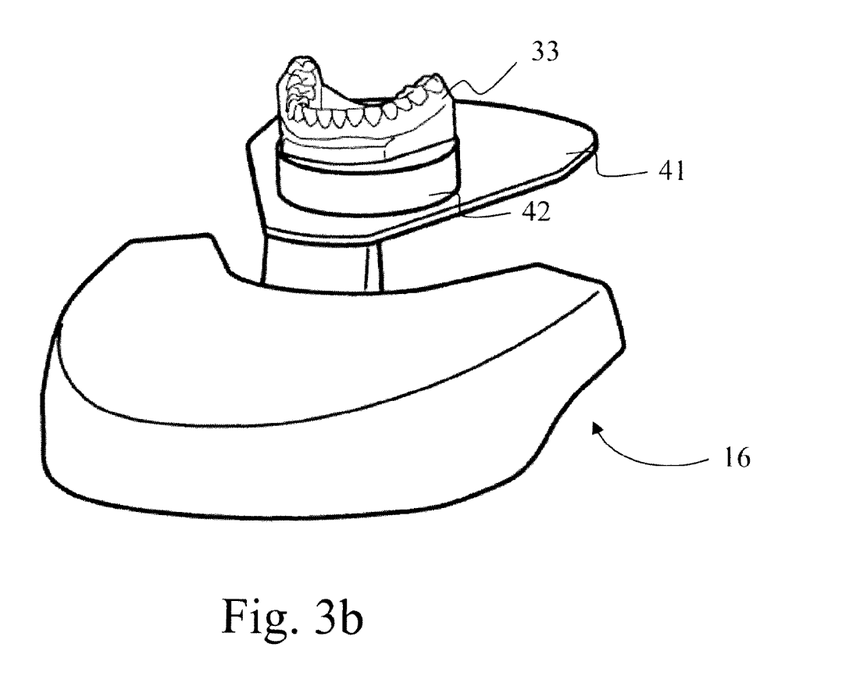

FIG. 3a shows a platform 41 for the physical tooth model 33 which can be selectively positioned, e.g., at the imaging station 16 of the apparatus 1 according to FIG. 1, and as shown in FIG. 3b the model 33 according to FIG. 2c can in turn be positioned or supported on that platform 41. Alternately, the impression 32 shown in FIG. 2b, together with the impression tray 31 or on its own, can be placed on the platform 41 for imaging. In the embodiment according to FIGS. 3a and 3b, the platform 41 is implemented such that it is selectively attachable to the imaging apparatus 1 in place of the bite block 17 shown in FIG. 1, designed for patient use. In this way, either the bite block 17 or the platform 41 may be selectively installed in the imaging station 16 at any one time. The platform 41 includes a stand 42 which, as well as the platform 41, may be made of material only weakly absorbs X-radiation and on top of which the impression 32 or the model 33 to be imaged can be positioned.

According to one embodiment, the platform 41 is implemented such that when installed in place of the bite block 17, it does not enable but rather purposely inhibits a patient from placing oneself at the imaging station 16 for imaging. Optionally, the imaging apparatus 1 is provisioned to detect or sense or otherwise know whether the bite block 17 or the platform 41 is installed at the imaging station 16. For example, means may be arranged to an attaching mechanism for attaching to the imaging apparatus 1, on the one hand, e.g. the bite block 17 and, on the other hand, the platform 41 to detect whether the bite block 17 or the platform 41 is attached to the apparatus. Such means may include a micro switch arrangement selectively detecting the bite block 17 or the platform 41 or, e.g., a pattern recognition system arranged to the imaging apparatus 1. Accordingly, the control system of the imaging apparatus 1 is optionally provisioned with a prevention function that inhibits the selection and/or use of imaging modes designed for imaging impressions and/or models 33 and/or other non-live and/or non-human subjects, if the bite block 17 or some other means for supporting and/or positioning a patient is installed at the imaging station 16. Besides or instead of this, the control system can be arranged to allow the selection and/or using of imaging modes intended for imaging specifically impressions and/or models 33 and/or other non-live and/or non-human subjects only when the imaging platform 41 arranged to hold, position and/or support them is installed at the imaging station 16, and/or only when otherwise particularly enabled.

Figure 4:
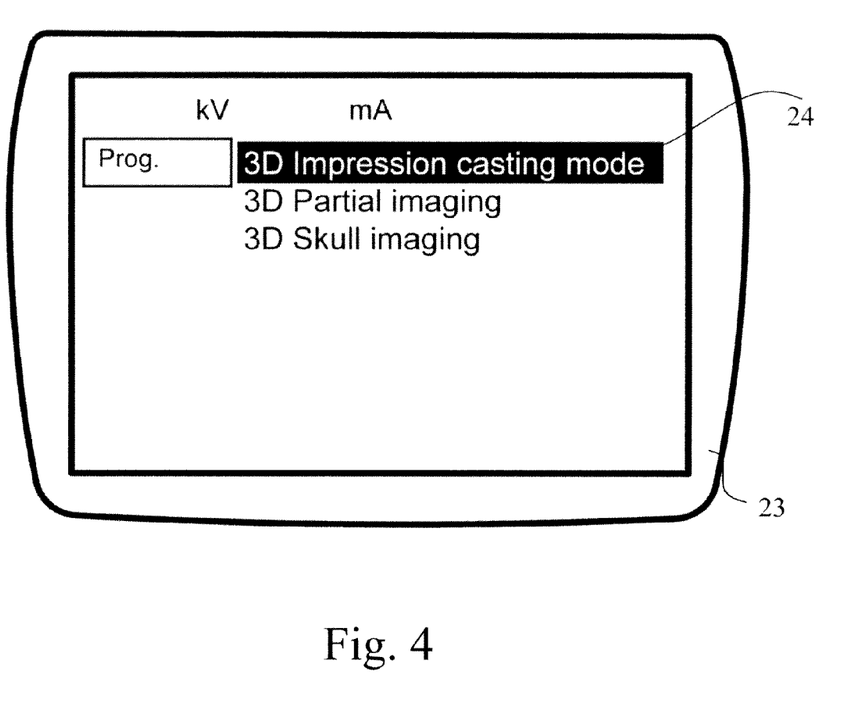
FIG. 4 shows a user interface attachable, e.g., to the apparatus of FIG. 1, including a selection menu or means for selecting an imaging mode for the apparatus.

FIG. 4 shows a user interface 23 which is attached, e.g., to the imaging apparatus 1 as shown in FIG. 1. Suitably, the user interface 23 includes a selection means 24 for selecting an imaging mode which is particularly intended for imaging impressions 32 and/or models 33 of teeth, or other non-live subjects. Suitably, this imaging mode is implemented to produce a 3D image of as high a quality as possible. Indeed, in this mode, an operator of the imaging apparatus 1 may optionally forego consideration of issues relating to radiation load which would tend to impose limitations for or on imaging parameter values, e.g., in contrast to when irradiating live patients where the radiation load to the patient should be a consideration.

Accordingly, one aspect of the present inventive subject matter pertains to the control system of the imaging apparatus 1 which is responsive to the selection of an imaging mode by an operator. For example, the control system is optionally provisioned such that in response to the selecting of at least one imaging mode (i.e., for non-live and/or non-human subjects such as impressions 32 or models 33), there results in a higher radiation dose being delivered to the object being imaged than would otherwise be delivered when selecting another imaging mode to be used for the imaging of a live patient. For example, in this second imaging mode, the control system may control any one or more or all of the following: (i) the operation of an actuator rotating the arm part 13; (ii) the operation of the source of radiation 14; (iii) the operation of the imaging sensor 15; and/or (iv) the operation of the collimator 18 and/or the filter 19; such that the object being imaged becomes imaged in a way which produces a substantially higher radiation dose than in the case of the selection of a live subject or patient imaging mode. In one suitable embodiment, at least one non-live subject imaging mode is provided and/or selectable (e.g., via the user interface 23) is which the control system of the imaging apparatus 1 functions to drive the actuator rotating the arm part 13 during exposure such that the source of radiation 14 and the imaging sensor 15 move at an angular velocity less than approximately 4 degrees/second. In yet another embodiment, the aforementioned angular velocity may be approximately 2 degrees/second or even slower. Optionally, if the imaging apparatus 1 is arranged with several imaging modes intended for imaging live patients, a non-live subject imaging mode according to another suitable embodiment may be additionally provided which would expose the imaged object to a substantially higher radiation dose than the largest of the doses associated with the imaging modes intended for imaging live patients. For example, in the non-live subject or non-human patient imaging mode, a radiation dose may be delivered to the imaged object which is of the order of at least twice as high as the highest produced by an imaging mode of the apparatus provided for imaging live patients. In yet another embodiment, a non-live subject imaging mode produces a dose area product (DAP) from the source of radiation 14 on a cross section with respect to a central axis of the beam, when considering a beam having an area of 0.02 m2 at a distance of 0.6 m from the focus of the source of radiation 14, which is larger than approximately 200 µGym2. Optionally, the aforementioned DAP is of the order of approximately 250 µGym2 or more. In still another embodiment, when in the non-live subject imaging mode, the radiation dose (Gray) produced by the source of radiation 14 substantially at the point of said imaging station 16 is of the order of approximately 40 mGy or more.

In one embodiment, an imaging mode exclusively intended for imaging impressions 32 and/or models 33 and/or other non-live subjects includes controlling the source of radiation 14 to produce intermittent or periodic pulses of radiation. On the other hand, the imaging mode optionally includes controlling the imaging sensor 15 such that, during exposure, more than approximately 500 images are taken each at different projection angles. For example, images may be taken at on the order of 1,000 different projection angles. Suitably, in this case, the source of radiation 14 and the imaging sensor 15 are rotated by an angle of approximately 200 degrees, while the approximately 1,000 images of the object from different projection angles within the approximately 200 degrees are obtained. It is also optional to implement the control system and/or movement of the imaging arm part 13 in the non live subject imaging mode so as to take projection images of the object by moving the source of radiation 14 and the imaging sensor 15 so slowly that during the taking of one image (i.e., during one irradiation pulse) a projection produced by the beam of a point or an item located in the object desired to be imaged moves on the imaging sensor 15 less than the dimension of a pixel of the imaging sensor 15 in the direction of movement of the imaging sensor.

In one other suitable embodiment, moving of the imaging means is arranged to comprise an imaging process lasting at least of the order of approximately 1 to 2 min, during which the source of radiation 14 and the imaging sensor 15 are moved through an angle of rotation of the order of approximately 200 to 360 degrees.

Odontological panoramic and computed tomography imaging typically employ imaging sensors having a pixel size smaller than actually would be required in these imaging applications. Hence, to decrease the need of processing an excessively large amount of data in such cases, it is quite typical that in connection with these imaging techniques the information of adjacent pixels is summed up before reading out the information from the imaging sensor or in connection with the read-out. With the non-live subject imaging mode described herein, there is little fear of the inanimate object being imaged moving during the imaging. Accordingly, the imaging time can be made to be long enough so that the image information of all the individual pixels can be read out during imaging. Thus, in one suitable embodiment, the information of adjacent pixels is not summed up before reading the information out or during reading. Optionally, the non-live subject imaging mode is also arranged to take projection images by moving the source of radiation 14 and the imaging sensor 15 at such a speed or otherwise in such a manner that the projection produced by the beam of a point or an item on the imaging sensor 15 located in the object desired to be imaged, e.g., moves during taking one image—or in the case of using pulsed radiation, alternatively during one irradiation pulse—at most a distance which equals the pixel dimension of the imaging sensor 15 in the direction of movement of the imaging sensor 15.

It is to be appreciated that in connection with the particular exemplary embodiment(s) presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein (e.g., such as the control system) may have their functionality suitably implemented via hardware, software, firmware or a combination thereof. For example, suitable software may include line of code or the like or other instructions contained on a computer readable media and executed by a microprocessor or the like to achieve the above-described functions, operations and/or control. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In any event, it is clear for those skilled in the art that one or more aspects of the present inventive subject matter may be implemented also in other ways than according to the embodiments described above. Indeed, the present specification has been set forth with reference to particular embodiments. Obviously, modifications and alterations will occur to others upon reading and understanding the present specification. It is intended that the invention be construed as including all such modifications and alterations insofar as they come within the scope of the appended claims or the equivalents thereof.

The invention claimed is:

1. An odontological X-ray imaging apparatus arranged to enable at least computed tomography imaging, the apparatus comprising:

an imaging station in which a selectively placed a subject being imaged by the apparatus;

a radiation source and a collimator structure which output x-ray radiation in a shape of a cone beam in a direction of the imaging station;

an imaging sensor including a two dimension array of x-ray detecting elements, said imaging sensor being arranged across the imaging station from the radiation source;

a construction including an actuator operative to rotate the radiation source and the imaging sensor about the imaging station, at least during an imaging exposure in which x-ray radiation is output from the radiation source and detected by the imaging sensor; and a control system for controlling operation of at least one of the actuator, the radiation source and the imaging sensor, according to at least one of two operative imaging modes, including a first imaging mode for imaging a subject's actual odontological anatomy and a second imaging mode for imaging a physical representation of a subject's odontological anatomy;

wherein when operating in the second imaging mode, the control system controls operation of said actuator during an imaging exposure so that said radiation source and said imaging sensor are rotated about the imaging station at an angular velocity of less than approximately 4 degrees/second.

2. The apparatus according to claim 1, wherein when operating in said second imaging mode, the control system controls operation of said actuator during an imaging exposure so that said radiation source and said imaging sensor are rotated about the imaging station at an angular velocity on en order of 2 degrees/second or slower.

3. The apparatus according to claim 1, wherein when operating in said second imaging mode, the control system controls said imaging sensor such that during an exposure, more than approximately 500 images are taken at different projection angles.

4. The apparatus according to claim 1, wherein when operating in said second imaging mode, the control system controls operation of said actuator during an imaging exposure so that said radiation source and said imaging sensor are rotated about the imaging station through a complete angle of rotation on the order of approximately 200 degrees.

5. The apparatus according to claim 4, wherein when operating in said second imaging mode, the control system controls said imaging sensor such that during an exposure, on the order of approximately 1,000 images are taken at different projection angles within the complete angle of rotation.

6. The apparatus according to claim 1, wherein when operating in the second imaging mode, the control system controls operation of said actuator during an imaging exposure so that said radiation source and said imaging sensor are rotated about the imaging station through a complete angle of rotation on the order of appropriately 200 to 360 degrees in an imaging process lasting at least on the order of 1 to 2 min.

7. The apparatus according to claim 1, wherein when operating in the second imaging mode, the control system controls the imaging sensor such that individual images are read out from the imaging sensor without summing up information of adjacent pixels before reading out the information or during read-out.

8. The apparatus according to claim 1, wherein when operating in the second imaging mode, the control system controls operation of said actuator during an imaging exposure so that said radiation source and said imaging sensor are rotated about the imaging station such that a projection on the imaging sensor produced by a beam of a point or item located in an object being imaged moves during taking one image at most a distance which substantially equals a dimension of a pixel of the imaging sensor in the direction of movement the imaging sensor.

9. The apparatus according to claim 1, wherein when operating in the second imaging mode, the control system controls an operation of the apparatus such that a dose area product (DAP) produced by the radiation source on a cross section with respect to a central axis of the beam, when considering a beam having an area of $0.02\ m^2$ at a distance of 0.6 m from a focus of the source of radiation, is larger than approximately $200\ \mu Gym^2$.

10. The apparatus according to claim 1, wherein when operating in the second imaging mode, the control system controls an operation of the apparatus such that a radiation dose (Gray) produced by the radiation source substantially at a location of said imaging station is on the order of approximately 40 mGy or more.

11. The apparatus according to claim 1, wherein when operating in the second imaging mode, the control system controls an operation of the apparatus such that a radiation dose produced by the radiation source is on the order of twice as high or higher than that produced when operating in the first imaging mode.

12. The apparatus according to claim 1, wherein the apparatus is arranged to receive at least one support comprising a platform positioned within the imaging station when the support is installed, said platform arranged to hold thereon the physical representation of a subject's odontological anatomy.

13. The apparatus according to claim 12, wherein said physical representation including at least one of a negative dental impression or a positive dental model.

14. The apparatus according to claim 12, wherein when the platform is positioned in the imaging station, it inhibits a subject from positioning their actual odontological anatomy substantially within the imaging station.

15. The apparatus according to claim 12, wherein said control system is implemented so that said second imaging mode is inhibited from selection when the support is not installed.

16. The apparatus according to claim 12, wherein said control system is implemented so that said second imaging mode is enabled for selection only when the support is installed.

17. The apparatus according to claim 1, wherein the apparatus is arranged to receive at least one support which positions a subject's actual odontological anatomy within the imaging station and said control system is implemented so that said second imaging mode is inhibited from selection when the support is installed.

18. The apparatus according to claim 1, wherein the control system is implemented such that said second imaging mode can be used only when specifically enabled.

19. An odontological X-ray imaging apparatus arranged to enable at least computed tomography imaging, the apparatus comprising:

an imaging station in which is selectively placed a subject being imaged by the apparatus;

a radiation source and a collimator structure which outputs x-ray radiation in a shape of a cone beam in a direction of the imaging station;

an imaging sensor including a two dimension array of x-ray detecting elements, said imaging sensor being arranged across the imaging station from the radiation source;

a construction including an actuator operative to rotate the radiation source and the imaging sensor about the imaging station, at least during an imaging exposure in which x-ray radiation is output from the radiation source and detected by the imaging sensor; and a control system for controlling operation of at least one of the actuator, the radiation source and the imaging sensor, according to at least one of two operative imaging modes, including a first imaging mode for imaging a subject's actual odontological anatomy and a second imaging mode for imaging a physical representation of a subject's odontological anatomy;

wherein said apparatus is arranged to receive a selected one of at least two supports, including a first support which positions a subject's actual odontological anatomy within the imaging station and a second support which posit ion physical representation of a subject's odontological anatomy within the imaging station, said physical representation including at least one of a negative dental impression or a positive dental model; and wherein when operating in the second imaging mode, the control system controls operation of said actuator during an imaging exposure so that said radiation source and said imaging sensor are rotated about the imaging station at an angular velocity of less than approximately 4 degrees/second.

20. A method for creating a three-dimensional digital model of one or more teeth, said method comprising:

obtaining a physical representation of a patient's teeth, said physical representation of the teeth being at least one of a three-dimensional negative impression of the teeth or a three-dimensional positive model of the teeth;

placing the physical representation of the teeth in an imaging station of an odontological X-ray imaging apparatus arranged and constructed for cone beam CT imaging of a live patient;

imaging said physical representation of the teeth by an imaging mode different from any imaging mode of the imaging apparatus arranged for the imaging of live patients; and generating the three-dimensional digital model of the teeth by processing image data detected upon imaging the physical representation of the teeth with the imaging apparatus.

21. The method of claim 20, wherein the imaging apparatus is selectively operable in one of two modes, including a first mode for imaging a live patient's actual teeth and a second mode for imaging the physical representation of the teeth, and the method further includes selecting the appropriate mode.

22. The method of claim 21, further comprising:

connecting a platform to the imaging apparatus, said platform arranged to hold the physical representation of the teeth within the imaging station.

23. The method of claim 22, further comprising:

detecting whether or not the platform is connected to the imaging apparatus; and automatically regulating an ability to select the second mode based on said detecting.

24. The method of claim 22, wherein when the platform is connected to the imaging apparatus, it at least partially inhibits a live patient from positioning their actual teeth substantially within a path of radiation extending through the imaging station.

25. A method of obtaining image data for creating a three-dimensional image of odontological structures, the method comprising:

providing an odontological X-ray imaging apparatus including a radiation source and an imaging sensor arranged at a distance from each other and rotatable about an imaging station, said apparatus being selectively operable in one of at least two modes including a first mode for imaging a subject's actual odontological anatomy and a second mode for imaging a physical representation of a subject's odontological anatomy, said physical representation including at least one of a negative dental impression or a positive dental model;

having selectively connected to the imaging apparatus one of a patient support device that supports actual odontological anatomy to be imaged within the imaging station or a platform that holds at least a portion of the physical representation to be imaged within the imaging station;

detecting if the patient support device or the plot form is connected to the imaging apparatus; and regulating an ability to select the operative mode of the apparatus based upon said detecting.

26. The method of claim 25, wherein operation of the apparatus in the second mode is inhibited if it is detected that the platform is not connected to the imaging apparatus.

27. The method of claim 25, wherein operation of the apparatus in the second mode is inhibited if it is detected that the patient support device is connected to the imaging apparatus.

* * * * *